US00PP14986P2

(12) United States Plant Patent
Lommerse

(10) Patent No.: US PP14,986 P2
(45) Date of Patent: Jul. 6, 2004

(54) DAHLIA PLANT NAMED 'KIEDAHBROV'

(50) Latin Name: *Dahlia variabilis*
Varietal Denomination: Kiedahbrov

(75) Inventor: Henry Lommerse, Mariahout-Laarbeek (NL)

(73) Assignee: Kieft Bloem zaden, B.V., Venhuizen (NL)

( * ) Notice: Subject to any disclaimer, the term of this patent is extended or adjusted under 35 U.S.C. 154(b) by 0 days.

(21) Appl. No.: 10/666,273

(22) Filed: Sep. 17, 2003

(51) Int. Cl.[7] ..... A01H 5/00
(52) U.S. Cl. ..... Plt./321

(58) Field of Search ..... Plt./321

(56) References Cited

PUBLICATIONS

UPOV–ROM GTITM Computer Database 2003/06, GTI Jouve Retrieval Software, Citation for 'Kiedahbrov'.*

* cited by examiner

*Primary Examiner*—Anne Marie Grunberg
*Assistant Examiner*—Annette H Para
(74) *Attorney, Agent, or Firm*—C. A. Whealy

(57) ABSTRACT

A distinct cultivar of Dahlia plant named 'Kiedahbrov', characterized by its upright, compact and rounded plant habit; freely basal branching habit; semi-double type inflorescences; and red purple-colored ray and disc florets.

1 Drawing Sheet

Botanical classification/cultivar designation: *Dahlia variabilis* cultivar Kiedahbrov.

BACKGROUND OF THE INVENTION

The present Invention relates to a new and distinct cultivar of Dahlia plant, botanically known as *Dahlia variabilis*, commercially referred to as a pot-type Dahlia, and hereinafter referred to by the cultivar name Kiedahbrov.

The new Dahlia is a product of a planned breeding program conducted by the Inventor in Venhuizen, The Netherlands. The objective of the breeding program is to create new pot-type Dahlia cultivars with desirable inflorescence form and attractive ray and disc floret coloration.

The new Dahlia originated from a cross-pollination made by the Inventor on Jul. 15, 1998 of a proprietary *Dahlia variabilis* selection identified as code number 96.2484, not patented, as the female, or seed, parent with a proprietary *Dahlia variabilis* selection identified as code number 96.2535, not patented, as the male, or pollen, parent. The new Dahlia was discovered and selected by the Inventor as a single flowering plant within the progeny of the stated cross-pollination in a controlled environment in Venhuizen, The Netherlands, during the spring of 1999.

Asexual reproduction of the new Dahlia by vegetative tip cuttings was first conducted in Mariahout-Laarbeek, The Netherlands during the summer of 1999. Asexual reproduction by cuttings has shown that the unique features of this new Dahlia are stable and reproduced true to type in successive generations.

SUMMARY OF THE INVENTION

The cultivar Kiedahbrov has not been observed under all possible environmental conditions. The phenotype may vary somewhat with variations in environment such as temperature and daylength, without, however, any variance in genotype.

The following traits have been repeatedly observed and are determined to be the unique characteristics of 'Kiedahbrov'. These characteristics in combination distinguish 'Kiedahbrov' as a new and distinct pot-type Dahlia:

1. Upright, compact and rounded plant habit.
2. Freely basal branching habit, full and dense plants.
3. Semi-double type inflorescences.
4. Red purple-colored ray and disc florets.

Compared to plants of the female parent, plants of the new Dahlia differ in inflorescence type and ray floret coloration as plants of the female parent have single inflorescences and lighter red purple-colored ray florets. Compared to plants of the male parent plants of the new Dahlia differ primarily in leaf coloration as leaves of plants of the male parent are lighter green in color.

Plants of the new Dahlia can be compared to plants of the Dahlia cultivar Dahlstar Violet, disclosed in U.S. Plant Pat. No. 12,755. In side-by-side comparisons conducted in Venhuizen, The Netherlands, plants of the new Dahlia and the cultivar Dahlstar Violet differed in leaf and ray floret coloration as plants of the cultivar Dahlstar Violet had lighter green-colored leaves and lighter red purple-colored ray florets.

BRIEF DESCRIPTION OF THE PHOTOGRAPHS

The accompanying colored photographs illustrate the overall appearance of the new Dahlia showing the colors as true as it is reasonably possible to obtain in colored reproductions of this type. Colors in the photographs may differ from the color values cited in the detailed botanical description which accurately describe the colors of the new Dahlia.

The photograph at the top of the sheet comprises a side perspective view of a typical flowering plant of 'Kiedahbrov'.

The photograph at the bottom of the sheet is a close-up view of a typical inflorescence bud, developing inflorescences, upper and lower surfaces of fully opened inflorescences, and the upper and lower surfaces of typical leaves of 'Kiedahbrov'.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown and flowered during the winter in Lompoc, Calif., under commercial practice in a polycarbonate-covered greenhouse with day temperatures about 18 to 24° C., night temperatures about 16 to 18° C., and light levels about 4,000 to 8,000 foot-candles. Rooted cuttings were planted in 15-cm container and plants were grown for about 14 weeks.

Botanical classification: *Dahlia variabilis* cultivar Kiedahbrov.

Parentage:

*Female, or seed, parent.*—Proprietary *Dahlia variabilis* selection identified as code number 96.2484, not patented.

*Male, or pollen, parent.*—Proprietary *Dahlia variabilis* selection identified as code number 96.2535, not patented.

Propagation:

*Type.*—Terminal tip cuttings.

*Time to rooting.*—Summer: About 8 days at 22° C. Winter: About 10 days at 22° C.

*Time to develop a rooted cutting:*—Summer: About 16 days at 20° C. Winter: About 20 days at 20° C.

*Root description.*—Fine to somewhat thick, fleshy; development of tubers has not been observed.

Plant description:

*Appearance.*—Herbaceous pot-type Dahlia. Inverted triangle; stems mostly upright and somewhat outwardly spreading giving a uniformly rounded appearance to the plant; relatively compact. Freely basal branching, about 12 lateral branches per plant; dense and full plants. Moderately vigorous growth habit.

*Plant height.*—About 22 cm.

*Plant width or area of spread.*—About 34 cm.

*Lateral branches.*—Length: About 17 cm. Diameter: About 4 mm. Internode length: About 1.5 to 2.2 cm. Strength: Strong. Texture: Smooth, glabrous. Color: 59A.

*Foliage description.*—Arrangement: Opposite; simple. Length: About 6.5 cm. Width: About 3.7 cm. Shape: Elliptical. Apex: Acuminate. Base: Acute. Margin: Serrate, irregular. Texture, upper and lower surfaces: Smooth, glabrous. Petiole length: About 2.5 cm. Petiole diameter: About 3 mm. Petiole texture, upper and lower surfaces: Smooth, glabrous. Color: Young and fully expanded foliage, upper surface: 147A. Young and fully expanded foliage, lower surface: 194A. Venation, upper surface: 186B. Venation, lower surface: 194A. Petiole, upper surface: 183D. Petiole, lower surface: 148C.

Inflorescence description:

*Appearance.*—Terminal and axillary semi-double type inflorescences held above and beyond the foliage on strong flexible peduncles; inflorescences face upright or outwardly. Composite inflorescence form with rounded elliptical-shaped ray florets and disc florets massed at the center; ray and disc florets develop acropetally on a capitulum. Inflorescences not fragrant. Inflorescences persistent.

*Flowering response.*—Plants flower continuous and freely from April until October in Northern Europe.

*Postproduction longevity.*—Inflorescences maintain good color and substance for about one week on the plant.

*Quantity of inflorescences.*—During the flowering season, about 60 inflorescences per plant may develop.

*Inflorescence bud* (*stage of showing color*).—Shape: Oblate. Length: About 1 cm. Diameter: About 1 cm. Color: 71B.

*Inflorescence size.*—Diameter: About 4.5 cm. Depth (height): About 2 cm. Diameter of disc: About 1.5 cm. Receptacle height: About 5 cm. Receptacle diameter: About 1.5 cm.

*Ray florets.*—Shape: Elliptical, rounded. Aspect: Straight, concave. Length: About 2.2 cm. Width: About 1 cm. Apex: Rounded, slight shallow point. Base: Attenuate. Margin: Entire. Texture: Smooth, glabrous, velvety. Number of ray florets per inflorescence: About 22 in about three rows. Color: When opening, upper surface: Slightly more red and brighter than 61A. When opening, lower surface: 64B to 64C. Fully opened, upper surface: Towards apex, 61B; towards base, 60A; color becoming closer to 75A towards the apex, 72C at the mid-section, and 60A towards the base. Fully opened, lower surface: 72C to 72D.

*Disc florets.*—Shape: Tubular, elongated. Apex: Five-pointed. Length: About 1 cm. Width: Apex, about 2.5 mm; base, about 1 mm. Number of disc florets per inflorescence: About 72. Color: Immature: 59B. Mature: Apex: 59A. Mid-section: 59B. Base: 1C.

*Involucral bracts.*—Quantity: About 20, imbricate. Length: About 1 mm. Width: About 4 mm. Shape: Elliptical. Apex: Rounded. Base: Truncate. Margin: Entire. Texture, upper and lower surfaces: Smooth, thin, membranous. Color, upper and lower surfaces: 147A.

*Peduncles.*—Length: About 7 cm. Diameter: About 2 mm. Strength: Strong, very flexible. Aspect: Upright. Texture: Smooth, glabrous. Color: 59A.

*Reproductive organs.*—Androecium: Present on disc florets only. Anther color: 23B. Pollen amount: Scarce. Pollen color: 23B. Gynoecium: Present on both ray and disc florets. Stigma color: 12A. Style color: 12C.

*Seed/fruit.*—Seed and fruit production has not been observed.

Disease/pest tolerance: Plants of the new Dahlia have not been observed to be tolerant to pathogens and pests common to Dahlias.

Weather tolerance: Plants of the new Dahlia have been observed to be wind and rain-tolerant; and have been observed to be tolerant to temperatures ranging from 12 to 30° C.

It is claimed:

1. A new and distinct cultivar of Dahlia plant named 'Kiedahbrov', as illustrated and described.

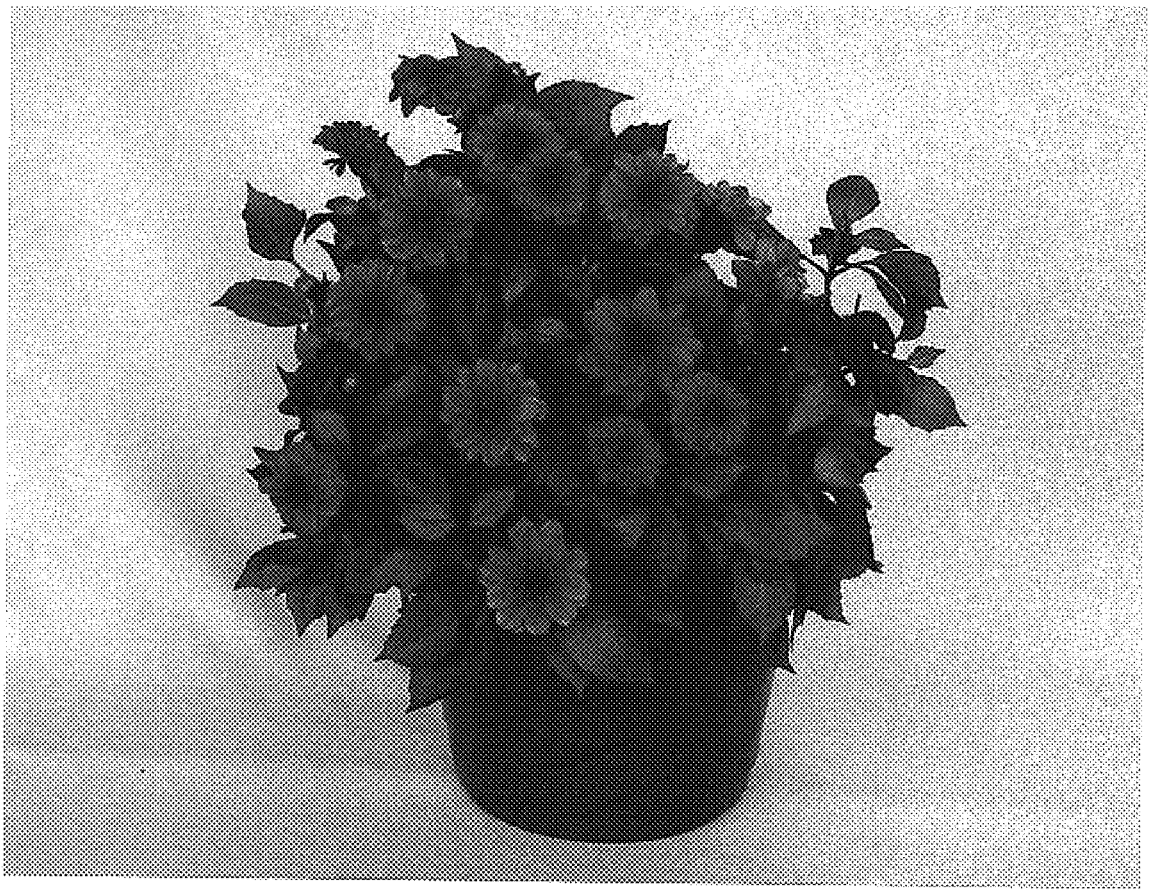
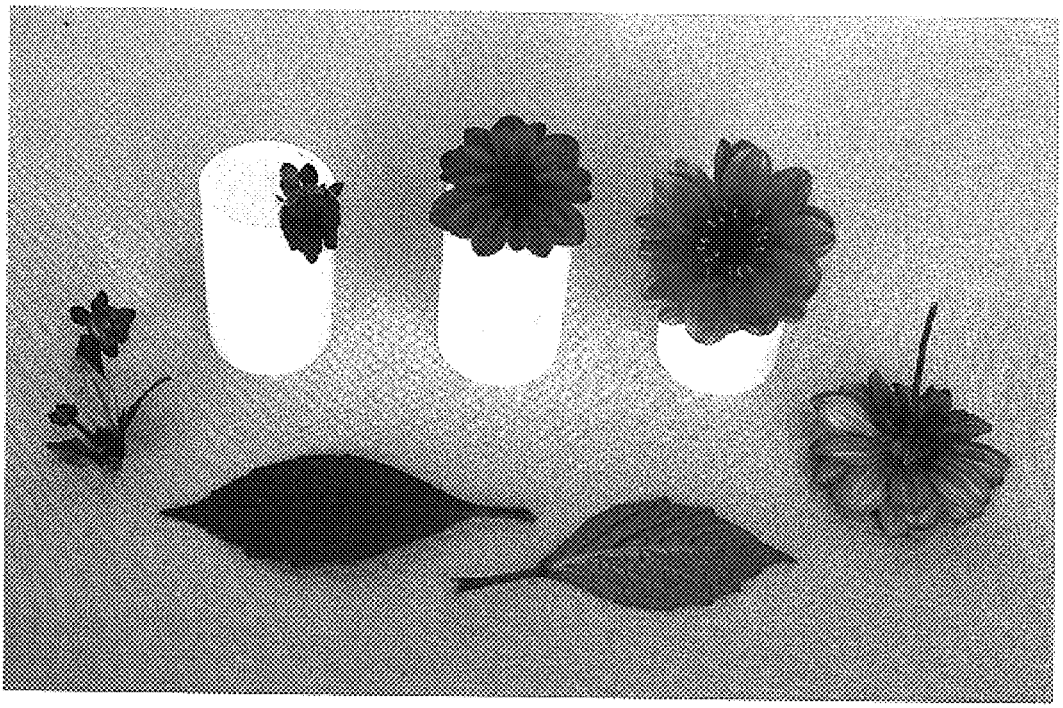

* * * * *